United States Patent
Furner et al.

(10) Patent No.: US 6,569,387 B1
(45) Date of Patent: May 27, 2003

(54) DUAL FUNCTION DISPENSER

(75) Inventors: Paul E. Furner, Town of Caledoia, WI (US); Heidi J. Uick, Town of Mount Pleasant, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/371,209

(22) Filed: Aug. 10, 1999

(51) Int. Cl.⁷ ............................ A62B 7/08; A61L 9/00; B67D 5/06; A24F 25/00; B05B 15/00
(52) U.S. Cl. .................. 422/123; 422/124; 422/125; 422/306; 222/183; 222/402.1; 222/402.13; 239/34; 239/43; 239/51.5; 239/53; 239/57; 239/289
(58) Field of Search ................. 422/123–125, 422/306; 222/183, 402.13, 402.1; 239/34, 43, 44, 47, 51.5, 53–55, 57–60, 289

(56) References Cited

U.S. PATENT DOCUMENTS

| | | | |
|---|---|---|---|
| 3,055,297 A | | 9/1962 | Leeds .......................... 101/327 |
| 3,946,945 A | | 3/1976 | Odioso et al. ................. 239/58 |
| 3,948,445 A | * | 4/1976 | Andeweg ..................... 239/53 |
| 3,972,473 A | * | 8/1976 | Harrison ...................... 239/34 |
| 4,084,732 A | * | 4/1978 | Dearling ................. 222/402.17 |
| 4,324,915 A | | 4/1982 | Roman ........................ 564/454 |
| 4,341,348 A | * | 7/1982 | Dearling ....................... 239/34 |
| 4,411,829 A | | 10/1983 | Schulte-Elte et al. ... 252/522 R |
| 4,434,306 A | | 2/1984 | Kobayashi et al. ......... 568/820 |
| 4,629,604 A | * | 12/1986 | Spector ....................... 422/124 |
| 4,726,519 A | * | 2/1988 | Muoio ......................... 239/49 |
| 4,759,501 A | * | 7/1988 | Silvenis et al. ................. 239/6 |
| 5,297,732 A | * | 3/1994 | Hahn ........................... 239/55 |
| 5,358,147 A | * | 10/1994 | Adams et al. .............. 222/183 |
| 5,364,027 A | * | 11/1994 | Kuhn .......................... 239/44 |
| 5,567,073 A | | 10/1996 | de Laforcade et al. ..... 401/190 |
| 5,788,155 A | * | 8/1998 | Martin et al. ................. 239/34 |
| 5,862,960 A | | 1/1999 | Miller et al. ................. 222/325 |
| 5,875,934 A | | 3/1999 | Miller et al. ................. 222/183 |
| 6,116,466 A | | 9/2000 | Gueret ........................ 222/94 |

FOREIGN PATENT DOCUMENTS

| | | |
|---|---|---|
| DE | 37 06 256 A1 | 8/1987 |
| WO | WO92/04419 | 3/1992 |

* cited by examiner

Primary Examiner—Robert J. Warden, Sr.
Assistant Examiner—Monzer R. Chorbaji (57) ABSTRACT

Disclosed herein are dispensers for dual functional use, wherein the dispensers are independently capable of dispensing a spray or an evaporative long term dispersible material. Also disclosed are refill units for such dispensers, which refill units comprise a spray can and associated control means, and an evaporative dispenser which may be activated by removal of a covering membrane which is impermeable to a volatile dispersible material. The spray and the evaporative volatile dispersible may or may not be the same material, permitting the consumer greater flexibility and choice.

21 Claims, 8 Drawing Sheets

DUAL FUNCTION DISPENSER

RELATED APPLICATION(S)

Not Applicable.

STATEMENT REGARDING FEDERALLY SPONSORED RESEARCH OR DEVELOPMENT

Not Applicable.

BACKGROUND OF THE INVENTION

1. Technical Field

The present invention relates to dispensers for dispersible compositions, such as fragrances and insect control materials. More particularly, the invention relates to active, or instant action, dispensers which are adapted for use with a replaceable cartridge containing a dispersible of choice, but are also capable of long term passive, or continuous, release of a dispersible substance. In one embodiment, the invention is related to devices for dispensing compositions, e.g. fragrances, etc., in two ways: actively, as a burst or spray of the chosen composition, to provide an immediate and intense air treatment; and passively, as an evaporative composition, to continuously effect the atmosphere over extended time periods at a slow release rate. The dispersible compositions to be dispensed by either the active dispensing means or the passive means may include such compositions as fragrances, air fresheners, deodorizers, odor eliminators, odor counteractants, insecticides, insect repellants, medicinal substances, disinfectants, sanitizers, mood enhancers, aroma therapy compositions, and the like. It is to be understood that odor eliminators include such odor absorbers as baking soda, zeolite, and charcoal, as well as more complex chemical odor eliminators, and that insecticides and insect repellants are examples of insect control compositions, which also include insect attractants or baits.

2. Background Art

The prior art is generally aware of dispensers for dispensing materials by way of an aerosol or pump activated spray dispenser into the air as minute droplets or spray, either while the dispenser is wall mounted, sitting on a level surface such as a table top, or hand held. Such active dispensers are frequently used for fragrances, or for air-freshening compositions. Adams et al, in U.S. Pat. No. 5,358,147, incorporated herein by reference, teach a spray dispensing package comprising an outer shell and a refill cartridge that fits therein and includes a spray valve, valve stem, and a spray nozzle. The outer shell has guide surfaces to cooperate with the refill cartridge to allow the shell to slide smoothly relative thereto when pressure is applied to the top surface of the shell to activate the spray valve. The materials most commonly dispersed by active dispensers include materials selected from the group consisting of fragrances, air fresheners, deodorizers, insecticides, and insect repellants.

In addition to such active dispensers, which require an action on the part of the consumer to result in the immediate dispensing of the dispersible composition, dispensers which operate passively, through evaporation or sublimation of vaporizable substances, without active physical participation by the consumer, are also well known. Such passive dispensers frequently comprise a porous, absorbent medium and an evaporation surface. Volatile dispersible substances frequently dispensed passively include fragrances, air fresheners, deodorizers, odor eliminators, malodor counteractants, insecticides, insect repellants, medicinal substances, disinfectants, sanitizers, mood enhancers, aroma therapy compositions, and other volatile materials easily dispersed by evaporation over an extended period of time. Such passive dispensing means, frequently utilizing a wick for liquid dispersibles, are well known in the prior art, as is the common type of dispensing device comprising a container retaining and/or supporting a body of gelatinous matter which, as it dries and shrinks, releases a dispersible composition into the atmosphere by evaporation or volatilization. Other passive products, such as impregnated plastic or ceramic substrates, or deodorant blocks, are also used to dispense air-treating vapors into the atmosphere by evaporation. Still other forms of such passive dispensers include liquid or gel cartridges which contain a dispersible substance which is time releasable through a porous covering of the cartridge, such as disclosed in U.S. Pat. No. 5,788,155 of Martin et al, the teachings of which are incorporated herein by reference. For purposes of the present invention, active dispensers shall be those which require an action on the part of the consumer to dispense a dispersible composition, which is dispersed as a burst or spray, as a direct result of the action of the consumer, while passive dispensers shall be those which require no action by the consumer, but dispense a dispersible by evaporation, sublimation, or the like, over a period of time, at a relatively low rate of dispersement when compared to the rate of dispersement of an active dispenser.

In the prior art, a number of attempts have been made to combine the features of active and passive dispensers, to provide the ability to both enhance the atmosphere with a burst of dispersible material for immediate effect, and to provide for a longer lasting, continuous, evaporative effect. An example of such an attempt is set forth in U.S. Pat. No. 3,972,473, of Harrison, which teaches a combined spray and evaporative air freshener comprising an aerosol container with a valve actuator and spray orifice so situated that spray from the aerosol is directed onto and collected by a shroud for the container. The liquid is allowed to collect in a cup, from which it slowly evaporates, or the liquid contacts an absorptive ring located within the shroud, which ring is activated by the spray to release a highly concentrated fragrance, etc. This arrangement, however, does not provide for immediate and direct release of dispersible substance into the atmosphere, unless the shroud and ring are removed from the dispenser. Another such dispenser, adapted for combined continuous and instant operation, is described in U.S. Pat. No. 5,364,027, of Kuhn, wherein a deformable container for a liquid dispersible substance is fitted with two immersion tube channels, one terminating in a spray nozzle, the other containing a wick or similar absorbent material providing for evaporation of the liquid. Also, Muoio, in U.S. Pat. No. 4,726,519, teaches a device for both instant and continuous dispensing of an air treatment composition. The device includes a pressurized container with a valve stem, an actuator-overcap, and an absorbent member adjacent to the walls of the overcap. By means for simultaneously spraying the air-treating liquid into the air and discharging it into the absorbent member, the device provides both simple spraying of the air freshener and recharging of a passive dispersal means (the absorbent member). Further, the device of Dearling, U.S. Pat. No. 4,084,732, may be manipulated and adjusted for simultaneous spraying into the air and recharging of a continuous dispensing means. In such prior art techniques, it has been found that formulations suitable for active dispersement, or spray usage, often were unsuitable for long term passive or continuous application, or vice versa. For example, the intensity of a dispersant may be suitable for one application method rather than the other, such as a material suitable for passive dispensing may have far too much intensity to be used as a spray. As a result, compromises were frequently necessary, which often resulted in the use of a formulation which was not fully suitable for either means of dispensing. Thus, the use of a single formulation to provide both instant and continuous effect usually resulted in compromising one or the other, or both.

These various devices of the prior art, incorporated herein by reference, have a number of practical problems and disadvantages which make them ineffective and unacceptable for use in the real world. For example, these dispensers all rely upon a single source or reservoir of dispersible material, and the continuous or passive dispensing is dependent upon the frequency and duration of use of the active dispenser. As a result, consumers generally do not accept these dispensers as being truly effective as either active or passive dispensers. Also, the consumer is unable to choose between differing dispersibles in a given dispenser. Further, a major problem relates to the dispensing habits of users of air fresheners, who frequently use aerosol sprays to overcome strong malodors, such as in bathrooms or kitchens, and are very accustomed to the intense and immediate nature thereof. On the other hand, while many people use continuous air fresheners or fragrancers in their homes, they generally are unaware of the manner in which they function, and frequently replace them at an inappropriate time, either before they have provided their full benefit, or maximum period of utility, or long after they have been exhausted and are thus ineffectual. Most often, one dispenser means would be exhausted or empty of dispersible material long before the other, causing the consumer to delay replacement or refill. For these reasons, among others, there is a need for dual function dispensers, or dual use dispensers of various forms of dispersible materials, which are simple to use, economically produced, and readily refillable by the ultimate consumer. In addition, there is a need for a dual use dispensing device for air treatment or other dispersible material dispensing which is not dependent upon recharging of the passive dispensing medium from the actively dispensed material, and in which the actively dispensed material and the passively dispensed material may be the same or differ, but under normal conditions of use will be fully dispensed in approximately the same period of time. That is, it is desirable that both materials be completely used up or expended at about the same time, so that the consumer will more readily recognize and react to the need for refilling, replacing, or disposing of the dispenser. Moreover, it is also possible for both the actively dispensed medium and the passively dispensed medium to be individually refillable or replaceable, so that the consumer may provide refills or replacements for one or the other as appropriate, or as individually desired, and so that the consumer may utilize differing materials in the two dispensing modes if so desired. It is to be understood, therefore, that the terms "dual use", "dual function", or "dual capacity" as used herein, are intended to designate dispensing systems for the dispensing of two or more independently released dispersible materials, from separate and independent sources or reservoirs.

SUMMARY OF THE INVENTION

An object of the invention is to provide a dual capacity dispenser for dispersible materials, said dispenser comprising the combination of an active dispenser for an actively dispersible material, said active dispenser comprising a reservoir containing said actively dispersible material, and means to actively dispense said actively dispersible material from said reservoir to the atmosphere; a passive dispenser for a volatile dispersible material, said passive dispenser comprising a reservoir containing said volatile dispersible material, and means to control volatilization of said volatile dispersible material; and a dispenser package encompassing said active dispenser and said passive dispenser, said dispenser package comprising a decorative body having a passage therein for dispensing said actively dispersible material from said active dispenser, and vent openings therein for passively dispensing said volatile dispersible material, said actively dispersible material and said volatile dispersible material being individually and independently dispensable.

An object of the invention is to provide a dispensing package for dispensing dispersible materials, said package comprising an outer shell, and a dispensing unit which fits within said outer shell, said dispensing unit comprising a spray can containing an actively dispersible material and means for dispensing said actively dispersible material, said dispensing unit further comprising a passive dispenser containing a volatile passively dispersible material, said passive dispenser having a membrane bonded thereto which is permeable to vapors of said volatile material, said outer shell being adapted to receive and cooperatively engage said dispensing unit and having vent openings therein corresponding to said permeable membrane.

A further object is to provide a dual capacity refill package for a dual function dispenser of dispersible materials, said refill package comprising a reservoir containing a spray dispersible material, means to spray such spray dispersible material, and an evaporative dispenser for a volatile dispersible material, said evaporative dispenser comprising a reservoir containing said volatile material, said reservoir having a membrane bonded thereto which is permeable to the gaseous form of said volatile material but impermeable to liquid or solid forms thereof, and a vapor impermeable membrane bonded to said reservoir containing said volatile material external to said permeable membrane to prevent volatilization of said volatile material and adapted for removal to permit volatilization of said volatile material.

Still another object of the invention is to provide a dual capacity dispenser for dispersible materials, said dispenser comprising the combination of an active dispenser for an actively dispersible material, said active dispenser comprising a reservoir containing said actively dispersible material, and means to actively dispense said actively dispersible material from said reservoir to the atmosphere; a passive dispenser for a volatile dispersible material, said passive dispenser comprising a reservoir containing said volatile dispersible material, and means to control volatilization of said volatile dispersible material; and means to combine said passive dispenser with said active dispenser to form a single unitary dual function dispenser.

It is thus an object of the present invention to provide a dual capacity dispenser for dispersible materials, which is able to simultaneously provide a burst of dispersible material into the air and to passively dispense the same material or a different material into the atmosphere by evaporation, over an extended time period. It is a further object of this invention to provide a dispenser which will be easily and conveniently refilled by the consumer upon exhaustion of the contents of one or both reservoir units of the dispenser, either by refilling or by replacing the reservoir unit for one or both dispersible materials. It is a still further object of the invention to provide a means by which the consumer may spray a dispersible substance into the atmosphere as desired, while providing a passive long-term continuous action fragrancing means. It is a still further object of the present invention to provide a dispenser in which the consumer may provide varying effect, by utilization of differing refill units or replacement units for both the actively dispensed material and the passively dispensed material. Still further, it is an object of the invention that the consumer be able to vary, at will and at his or her own discretion, the contents of either or both of the dispensing modes of the dual capacity dispenser of this invention.

These and still other objects and advantages of the present invention will be apparent from the description which follows. While the description which follows frequently refers to an air freshener or fragrancing application, it is to be understood that the invention is also applicable to other forms of dispersible materials which may be dispensed either actively or passively, such as deodorizers, odor eliminators, malodor counteractants, insecticides, insect repellants, medicinal substances, disinfectants, sanitizers, mood enhancers, aroma therapy compositions, and the like.

It is also to be understood that while this specification is written in terms of dual use, i.e. two modes of operation, it is within the scope of the invention to use three or more individual dispensers within the context of a single multiple use apparatus. Thus, the invention may encompass a dispenser comprising a single active dispenser for providing a rapid burst of dispersible material, with two or more associated passive dispensers, said dispensers containing the same or different dispersants, for long term passive, evaporative dispensing of dispersible materials. Further, the term active dispenser, as used herein, is intended to encompass, without limitation, all forms of rapid dispensers, inclusive of pressurized, aerosol, bellows, air displacement, and pump action dispensers. While these dispensers are frequently cylindrical in shape, with a spray nozzle or control at the top, it is understood that various configurations and shapes of such active dispensers are equally suitable. Likewise, the term passive dispenser, as used herein, is intended to encompass, but not be limited to all forms of passive dispensers, including gel cartridges, impregnated porous structures, and evaporative liquid dispensers including those utilizing wicking and evaporation, with or without heat or other means to increase rates of vaporization, such as fans. As previously indicated, active dispensers are to be considered those in which a positive action is required by the consumer to obtain dispensing of the dispersible material, said action constituting more than opening of a package, removal of a vapor inhibiting barrier, or turning on a fan or heating element. The following description is merely of the preferred embodiments, provided in terms of air freshening or fragrancing for convenience, and the claims should be looked to in order to understand the full scope of the invention.

BEST MODES FOR CARRYING OUT THE INVENTION

Figure 1:
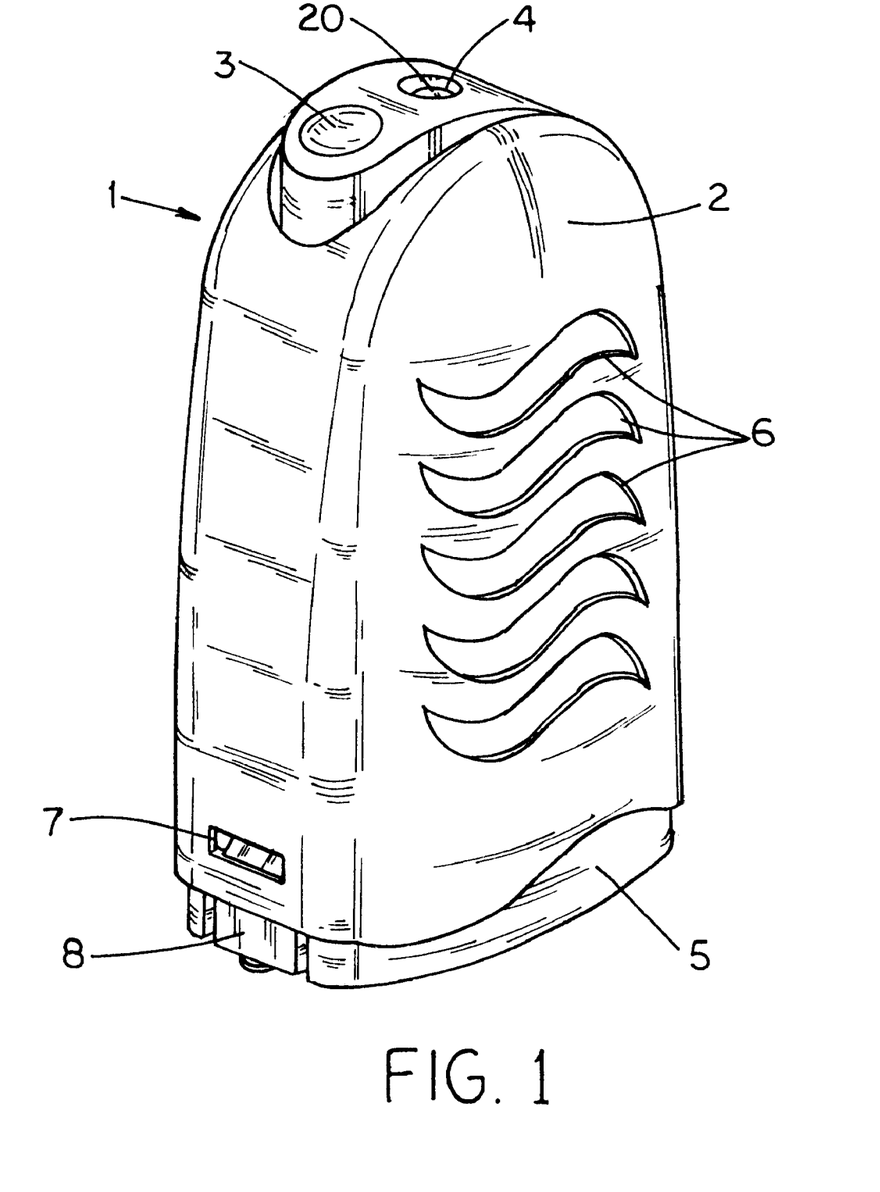
FIG. 1 illustrates a perspective view of one example of a dual capacity dispenser of the present invention.

The dispenser illustrated in FIG. 1 represents a typical configuration of a dispenser of the present invention. Shown is a dispenser, 1, comprising a shell or shroud, 2, a spray control button, 3, a spray tip 4, having spray nozzle orifice 20, and a base, 5, which is joined to shell 2 by means of cooperative latch mechanism 8 and latch opening 7. Vent openings, 6, are cut through the shell, permitting air flow to and from the interior of the shell.

Figure 2:
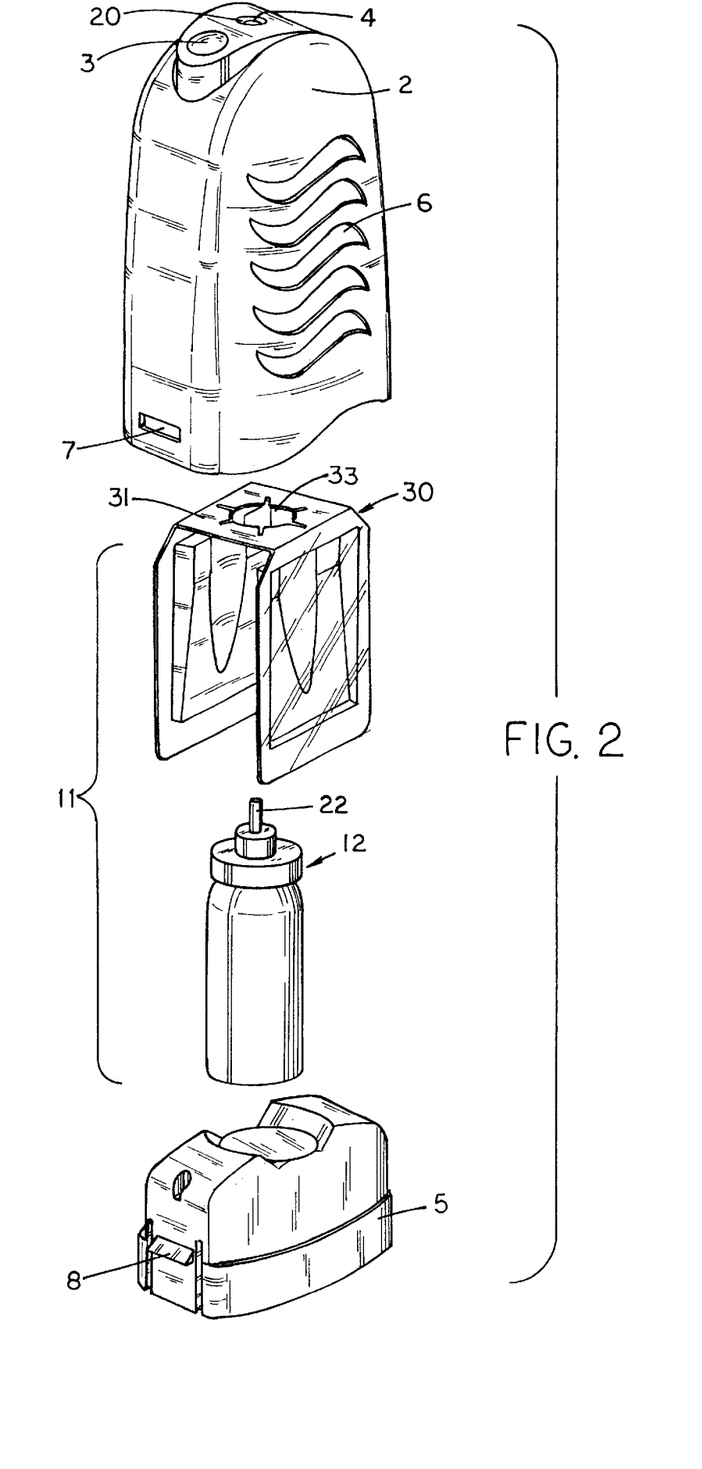
FIG. 2 illustrates an exploded sectional view of the dual capacity dispenser of FIG. 1, showing the relationship of various components thereof.
Figure 7:
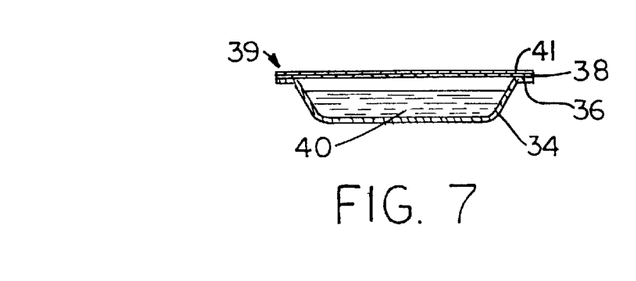
FIG. 7 represents a sectional view of the cartridge of FIG. 6, taken along lines 7—7 of FIG. 6.
Figures 8, 9, 10, 11:
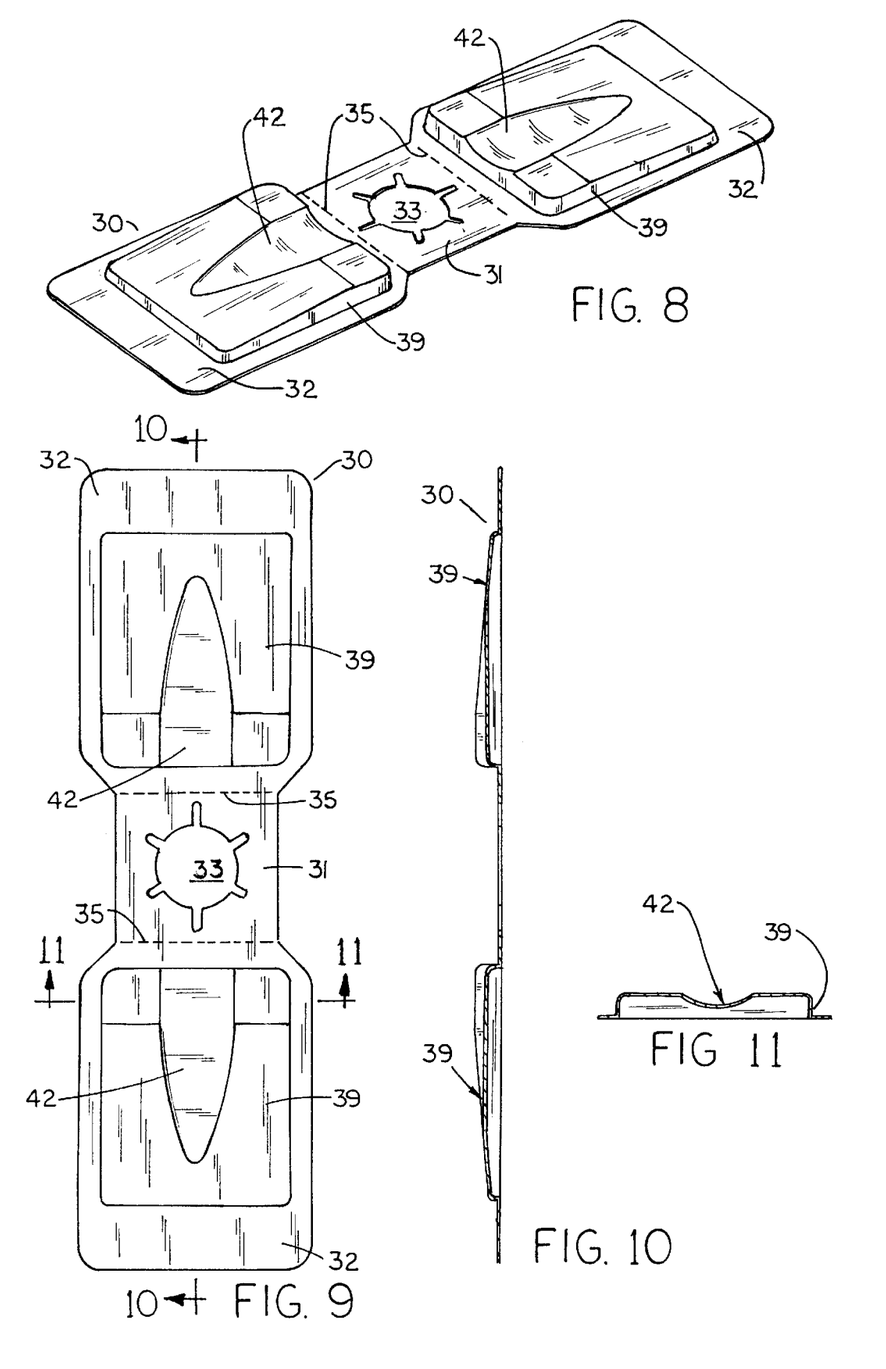
FIG. 8 illustrates a perspective view of a preferred embodiment of a twin gel cartridge refill assembly, illustrating the relationship of the gel reservoirs.
FIG. 9 illustrates the top view of the twin gel cartridge of FIG. 8.
FIG. 10 is a sectional view of the cartridge of FIG. 9, taken along lines 10—10 of FIG. 9.
FIG. 11 is a sectional view of the cartridge of FIG. 9, taken along lines 11—11 of FIG. 9.

As shown in FIG. 2, the enclosure shell, or shroud, 2 encloses a dual capacity refill unit 11, comprising a spray container 12, and a gel cartridge dispenser 30. The shell or shroud, 2, is the exterior surface of the dispenser, and as such is subject to visual inspection as well as being picked up and handled during spray dispensing. Accordingly, the shell is desirably visually attractive and of suitable dimensions that it may be left in view in the area of usage for greatest effectiveness during evaporative dispensing. Preferably, the shell is constructed of a durable, but economical, material such as plastic, glass, or ceramic. The gel cartridge 30 is preferably a twin cartridge air freshener device of the type taught in U.S. Pat. No. 5,788,155, of Martin et al, incorporated herein in its entirety by reference. Such an air freshener device comprises a pair of cartridge units connected end-to-end by a flexible hinge portion, 31, adapted to engage, via centering hole 33, the spray stem, 22, of a spray container, 12, and thus engaged, to lie in parallel contiguous relationship to the lengthwise dimension of said spray container. Thus positioned, as shown in FIGS. 2–5, the gel cartridges overlay a substantial portion of the diameter and length of said spray container, with the passive dispenser units on opposed sides of said spray container, preferably proximate to the vent openings, 6, of the shell or shroud, 2. It is to be noted that the vapor permeable side of the gel package faces to the outside, i.e. away from the spray container, so as to obtain the greatest available permeation and flow of the volatile gel material through the permeable surface to the atmosphere. FIGS. 6–10 illustrate suitable embodiments of a passive dispenser unit of the invention, with FIGS. 8–10 illustrating a preferred embodiment.

While the illustrations and the text of this description of the invention speak in terms of twin gel cartridge units, it is to be understood that any number of twin or individual passive dispensers may be used, spaced about the diameter of the active dispenser container as desired, and comprising passive dispensers of types other than gel dispensers, such as liquid containing cartridges, impregnated plastic evaporative units, impregnated paper units, blotters, etc. It is also to be understood that a single gel cartridge or passive dispenser unit may be employed, located so as to abut one side of said spray container and shell assembly, and to lie between said spray container and said shell, positioned properly either by means of a cooperative fitting with the spray tip assembly of said spray container and said spray container, positioning ribs or protrusions on the inside of the shell, or a combination of such means. It is understood that the shell or shroud of the dual capacity dispenser is preferably an enclosure for the active and passive dispenser units, and as such thus creates an evaporation space for the passive dispenser, which evaporation space communicates with the atmosphere by way of the vents, 6. The shell may be structured so as to have internal ribs and or protrusions to cooperatively engage the active dispenser or the passive dispenser, or both, thus providing means by which the consumer is prevented from improper placement of the dispensers within the shell. When twin gel cartridge units, or plural single cartridge units, are employed, they may contain the same or differing dispersible materials, and the consumer may activate any or all of said cartridges at his or her option, by removal of outer impermeable barrier membranes over the surfaces thereof, prior to engagement with the shell. Thus, the consumer may choose to utilize only one passive dispenser unit at a time, providing longer life for the passive dispenser. Alternatively, the consumer may choose to use multiple passive dispenser units simultaneously, providing additional strength, or if differing dispersible materials are employed, providing a blend of the consumers choice. It is also to be understood that the passive dispenser means may lie outside the shell or shroud, or may be attached directly to the active dispenser in the absence of a decorative shell or shroud, as shown, for example, in FIGS. 12–19. It also possible for the performance of the passive dispenser to be enhanced, by such means as provision of a fan to more rapidly draw air across the surface thereof, or by heating so as to cause more rapid evaporation.

Figure 3:
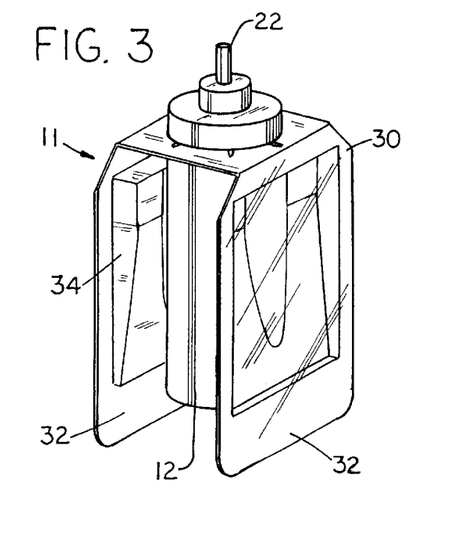
FIG. 3 illustrates a dual capacity refill unit for the dispenser of FIGS. 1 and 2, said refill unit comprising a spray cartridge for active release of a dispersible, and a gel cartridge assembly for passive release of a dispersible. The continuous acting or passive dispersible is shown as provided in the form of a twin cartridge which is configured so as to fit across the top of the active dispenser in accordance with the present invention.

FIG. 3 illustrates the combination of the individual components of a dual capacity refill cartridge, 11. As shown, the gel cartridge assembly, 30, constituting a twin cartridge dispenser unit, is centered upon the spray container 12, and hangs downwardly on both sides thereof. Each gel cartridge, 32, comprises an elongated shallow tray, 34, providing a reservoir for the storage of a volatile medium, with a thin permeable membrane sealing said reservoir enclosure, a volatile dispersant medium in the reservoir enclosure, and a thin removable impermeable membrane which is laminated coextensively with the permeable membrane to prevent premature volatilization of the dispersant.

Figure 4:
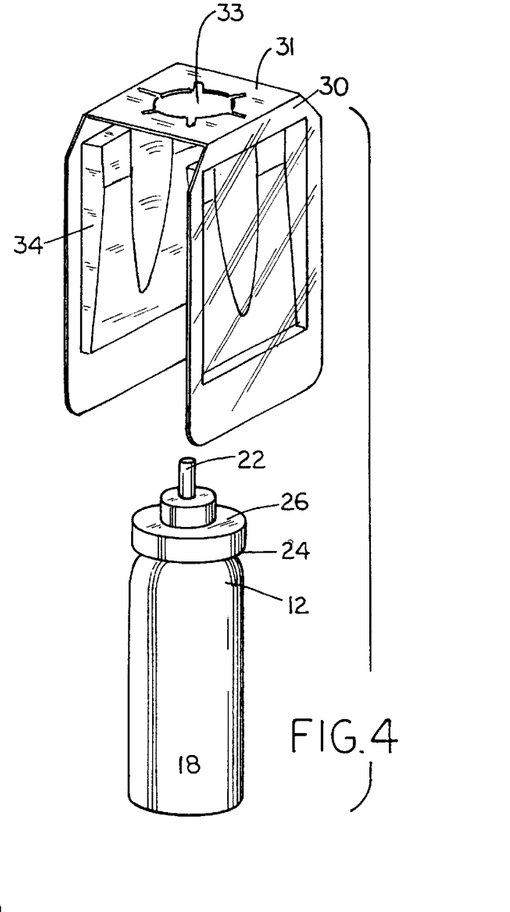
FIG. 4 represents an exploded detail of the dual capacity refill unit of FIG. 3, illustrating in greater detail the relationship of a preferred embodiment of a passive dispenser to the active dispenser of FIGS. 2 and 3.

FIG. 4 further illustrates the relationship of the component parts of a dual capacity refill unit, in exploded view, showing the gel cartridge 30, which is configured to be fitted across the top of the spray container 12, by means of centering hole 33 in central portion 31, designed to pass over the top surface, 26, of the spray valve body, so as to come to rest in a force fit against the upper vertical sides of the spray container. The spray container, 12, as illustrated, comprises a reservoir can 18, formed from a can body onto which a standard spray valve, such as an aerosol valve which may be a metering valve, or a pump spray valve, having valve stem 22, is located by means of valve crimp 24. The spray valve body has a top surface 26, which is useful in centering the spray can in the shroud or shell into which the spray can is inserted either as a refill or as the initial spray container. When positioned within the shroud or shell, the spray can 18, having valve stem 22, is in fluid communication with spray nozzle orifice 20, via spray tip 4 as seen in FIG. 2. The spray valve is appropriately actuated by such means as a spray button, 3, as shown in FIGS. 1 and 2, or by such other actuation means as may be selected by one skilled in the art. In operation, the spray control button 3 is depressed, actuating the spray container 12, upon demand. This results in a spray of dispersant being released from the spray container as desired, to provide an immediate effect or to increase the potency of dispersible available to the consumer. It is preferred that the spray container be controlled by a dosage measuring spray valve, such that a specific amount of dispersant is released from the spray container at each actuation. In such actuation control, merely holding the spray button down does not result in a continuous spray of dispersible from the container, which is wasteful and less efficient than controlled dosage spraying. In addition, the gel cartridge dispenser releases dispersible at a predetermined and essentially constant rate, by evaporation, as a result of the vapor impermeable membrane having been removed, or peeled, from the cartridge gel reservoirs, 34. The dispersible gel, which may be any of those known in the art, is restrained within the cartridge by a thin vapor permeable membrane, which permits evaporation of the dispersible at a pre-established rate.

Figure 5:
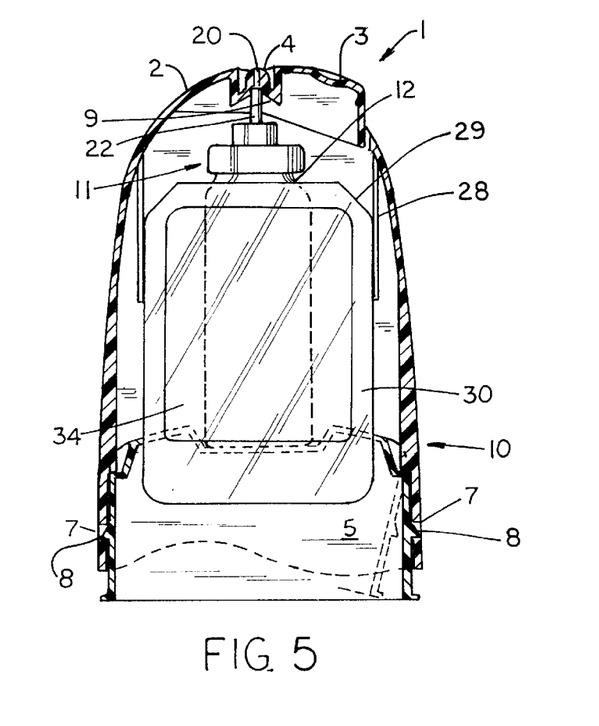
FIG. 5 represents a cross sectional view of the dispenser of the present invention showing the relationship of the outside shell or case to the dual capacity refill unit of FIG. 3.

FIG. 5 represents a cross sectional view of a dual capacity dispenser of the present invention. The dispenser, 1, comprises shell 2, base 5, and a dual capacity refill unit 11, which in turn comprises spray container 12, and gel cartridge passive dispenser 30, having gel reservoir 34. The shell comprises a spray control button 3, with a spray tip 4, having spray nozzle orifice 22 therein aligned with the valve stem 22 of the spray container. The shell interlocks with base 5 by means of latch opening 7, which aligns with the base latch opening 8. As illustrated, shell 2 also incorporates chamfer means 9, to receive and position valve stem 22 of the spray container as it is inserted into the shell, thus assuring proper alignment, as well as stop means, 10, to abut base 5, to prevent the consumer from attempting to push the base and refill unit too far into the shell. Also illustrated are rib protrusions 28, inside the shell, positioned to cooperatively engage the chamfered portion 29 of the gel cartridge, so as to properly align the gel cartridge with the face of the shell and with the centrally located spray container 12. By this arrangement, the consumer is assured of being able to simply and correctly insert a fresh dual capacity refill unit into the shell and base assembly of the dispenser as desired or as necessary. Of course, the consumer may also choose to insert only one individual refill unit rather than both an active dispenser and a passive dispenser, if desired, thus replacing only the active dispenser, or only the passive dispenser, at will.

The prior art is generally aware of aerosol dispensers for dispensing pressurized materials into the air. See, for example, Adams et al, U.S. Pat. No. 5,358,147, Miller et al, U.S. Pat. No. 5,862,960, and Miller et al, U.S. Pat. No. 5,875,934, all of which are incorporated herein by reference. These references relate to aerosol dispensers having refill cartridges for dispensing such compositions as perfumes into the air as an air freshener, or insect control ingredients for home use. Such dispensers comprise an aerosol can to contain a pressurized material to be dispensed, a nozzle having a delivery tube in fluid communication with the can and a spray orifice through which the pressurized material can escape from the delivery tube, and valve means for controlling the release of the pressurized material into the nozzle delivery tube. In addition, PCT published Application WO92/04419 discloses aerosol compositions packaged within a metering valve aerosol having a high level of perfume. Formulations and metering valves such as described in this patent can be used in the device of the present invention. Of particular utility in the present invention are those aerosol cartridges which fit within the outer shell of the presently described dispenser, the refill cartridge including a spray container having a can body and a valve including a valve stem, such as described by Adams et al, U.S. Pat. No. 5,358,147. The use of metering or metered dosage valves is of particular value, permitting the dispenser of the present invention to enable the consumer to employ a predetermined spray volume or dosage, and to utilize the spray feature of the present invention for a predetermined number of applications. It has been found to be particularly useful to use a spray dispenser having a container of approximately 60 to 200 ml capacity, preferably about 120 ml capacity, with a metering valve which dispenses from about 50 to about 250 sprays, preferably from about 60 to about 150, and most preferably from about 90 to about 100 sprays from the container before the container is empty or exhausted, dependent upon the needs and/or usage patterns of the consumer.

Figure 6:
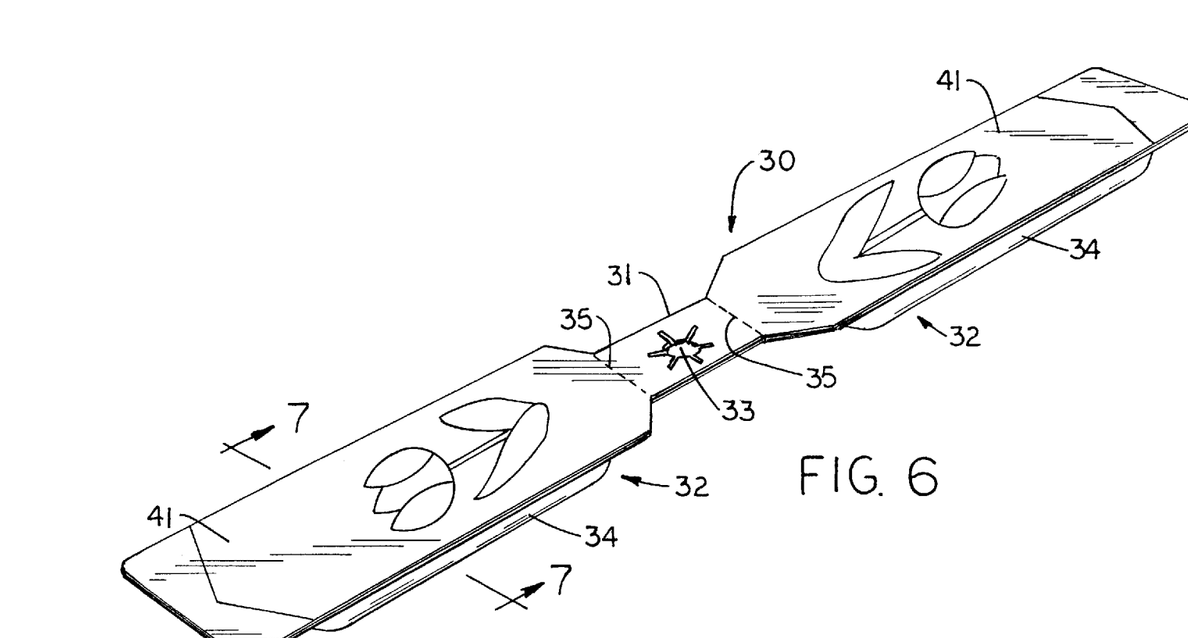
FIG. 6 represents an example of a gel cartridge assembly suitable for use in the dispenser of the present invention, comprising twin cartridges connected end-to-end with a flexible hinge means, shown with the removable membrane in place over the twin gel reservoirs.

FIG. 6 represents an example of a gel cartridge assembly suitable for use in the dispenser of the present invention, viewed from the side of the removable impermeable membrane which seals the reservoir enclosure shut. The twin cartridges, joined end-to-end by flexible central hinge portion 31, having a centering hole 33 therein, may be folded over at seams 35, and fit over the top of a spray container, 12, the cartridges extending downwardly parallel to the length of the spray container, as illustrated in FIGS. 2–5. While FIG. 6 illustrates an air freshener cartridge device suitable for use in the present invention having a design printed upon the impermeable membrane which is removed to activate the cartridge or cartridges, it is understood that no such design is necessary. As illustrated in FIGS. 6 and 7, each of such twin cartridges, 32, is a structural assembly comprising an elongated shallow tray, 34, having side walls with an upper edge flange, 36, which forms a peripheral margin around the open space of the tray, with a thin membrane, 38, which covers the open space of the tray 34 and is bonded to the flange peripheral margin. The membrane 38 forms a sealed reservoir enclosure 39 within the tray interior, said membrane, 38, being permeable to the vapor form of the volatile medium, 40, which is contained within the reservoir enclosure, but not the liquid or solid form. A thin, peelable, impermeable membrane, 41, is laminated coextensively with the permeable membrane to prevent volatilization of the dispersant medium through the permeable membrane 38, from the reservoir enclosure, 39, prior to the intended utilization of the cartridge. Activation of the cartridge is accomplished by removal, e.g. peeling, of the impermeable membrane 41. A gel cartridge dispenser, 30, such as shown in FIG. 6, has a semi-rigid structure, and may be typically about eight inches in length, about one half to one inch in width, and about one sixteenth to one half inch in thickness. A preferred volume of such a cartridge is sufficient to hold from about 2 to 4 grams of gel, but the volume may vary to contain from 0.5 to about 10 grams of gel. Such a dispenser may be utilized by peeling the outer impermeable membrane, 41, partially or completely from one cartridge, or peeling said outer impermeable membrane from both of the twin cartridges, and folding the dispenser at seam lines 35 of hinge 31 so as to place the twin cartridges approximately parallel to each other, and inserting the valve stem, 22, and the top surface of the spray valve body, 26, of a spray can, through hole 33, so as to drape the passive dispenser down both sides of said spray can. It is clear that the reservoir enclosure may take a variety of shapes, and that various configurations thereof are possible, such as having ribs therein which serve both to reinforce the enclosure and to key the enclosure into a conformational slotted space in the dispenser shell. It is also evident that single reservoir cartridges may be provided, in which only one reservoir of dispersant is present, which may be utilized in alternative forms of dual capacity dispensers, or in the dual capacity dispenser of FIGS. 1 and 5, suitably modified for acceptance of such a single reservoir passive dispenser.

As illustrated in FIGS. 8–11, a preferred cartridge assembly may be configured to fit the side of the active spray container 12. As shown, the twin gel cartridge 30, comprises a pair of reservoir enclosures 39 adjacent to a central hinge portion having centering hole 33 and folding seams or hinge points 35. To enable the individual dispenser cartridges to conform to the spray container when the twin gel cartridge dispenser is folded and placed over the top thereof, the reservoir enclosures are provided with a conforming configuration, 42, shaped to fit about the side of the spray container and to accept the circumference thereof. It has also been found advantageous that the cartridges angle slightly outwardly from top to bottom of the spray container, at an angle of about 7 degrees from the vertical as measured at the hinge point of the cartridge. This angle assists in holding the refill unit in position in the shell, and contacting more of the content of the cartridge tray with the permeable membrane, as well as bringing the permeable membrane in closer proximity to the vent area of the shell or shroud of the dispenser. The area of the shell which is cut away or removed to form the vent area should be in proximity to the dispensing area of the cartridge, i.e. the area of permeable membrane which is uncovered by removal of the impermeable surface membrane. Further, it has been found advantageous that the open area of the vents correspond to approximately 25 to 90 percent, preferably 40 to 60 percent, and most preferably 45 to 55 percent of the surface area of the permeable membrane through which the dispersant is released, to achieve control of the rate of release of the dispersant so as to maintain the desired dispensing life. It is desired that the dispenser have a useful life span of up to two months, about 60 days, preferably about one month, or thirty days. While this rate of dispensing may, alternatively, be controlled by selection of the porosity of the permeable membrane and the volatility of the dispersant, it has been found that control of the vent surface area ratio, i.e. the ratio of the area of the open vent in the shell to the area of the exposed permeable membrane, is the simplest manner in which one may directly effect the length of time that the cartridge will continue to dispense vapor. That is, the greater the amount of vent area aligned with the dispensing surface of the passive dispenser, the more rapidly said passive dispenser will disperse its volatile content. It is also considered feasible that the vent area be adjustable, by such means as sliding members which control the area of vent opening which is open or closed, so as to permit more or less rapid evaporation of the content of the cartridge, in accordance with the personal preference or needs of the consumer. An example of such a sliding member would be a plastic plate conforming to the inside of the shell proximate the vent openings, and adapted to be displaced either vertically or horizontally so as to adjust the area of vent openings which are open for circulation of air from the interior to the exterior of the shell.

The elongated tray, 34, may be constructed by either injection or thermoform molding of a thermoplastic polymer such as polyethylene, polypropylene, polyvinyl chloride, and the like. In a preferred embodiment, end-to-end attached trays 34, and interconnecting flexible hinge band 31, are thermoformed as a unitary structure, and preferably include folding seams 35 to facilitate a 90 degree fold. The thin film vapor-impermeable membrane 41 is bonded to thin film vapor-permeable membrane 38 in the form of a laminate. Vapor-impermeable film 41 is peelable, so that its removal allows volatile dispersant ingredient 40 to migrate through vapor-permeable membrane 38 and volatilize into the atmosphere. Removable or peelable membrane 41 can be adapted for removal from both cartridge units at the same time, or from each cartridge unit independently. Vapor-permeable membrane 38 can be in the form of a flexible thin film of a thermoplastic polymer such as polyethylene, isotactic polypropylene, cellulose acetate, and the like. Membrane 38 permits migration of the enclosed volatile dispersant ingredient 40, either as a liquid or a vapor, depending on the type of membrane employed. Membrane 38 may be a microporous type, having submicron pores, such as isotactic hydrophobic polypropylene film sold under the tradename CELGARD, by Celanese, Inc. Microporous thermoplastic polymer films are described in U.S Pat. No. 3,055,297, incorporated herein by reference. It is also advantageous that the vapor permeable membrane, 38, which encloses the dispersible material in the gel cartridge be transparent, or minimally opaque, so as to permit observation of the contents of the reservoir enclosure by the consumer, so as to permit the consumer to judge the remaining life span of the cartridge, and thus to observe when replacement is appropriate. This is also true for cartridges in which the passive dispersible is in the form of a liquid rather that a gel.

Vapor impermeable membrane 41 may be in the form of a flexible thin film such as aluminum foil or nylon film, which is peelable from its adhering bond to vapor-permeable membrane 38. In a preferred embodiment, a laminate of membrane 41 and membrane 38 is preformed, and then applied to tray 34 to cover the open interior, and heat-sealed along periphery flange 36 to enclose the reservoir content of dispersible ingredient 40. The dispersible ingredient 40 can be any dispersible material which can migrate through membrane 38 and disperse into the atmosphere in vapor form.

In addition to the configurations illustrated in FIGS. 1–11, it is possible to provide dispensers such as illustrated in FIGS. 12–19, wherein the passive dispenser may be attached directly to the spray container, or to the decorative shell itself, or to an overcap for the spray container, for example.

Figure 12:
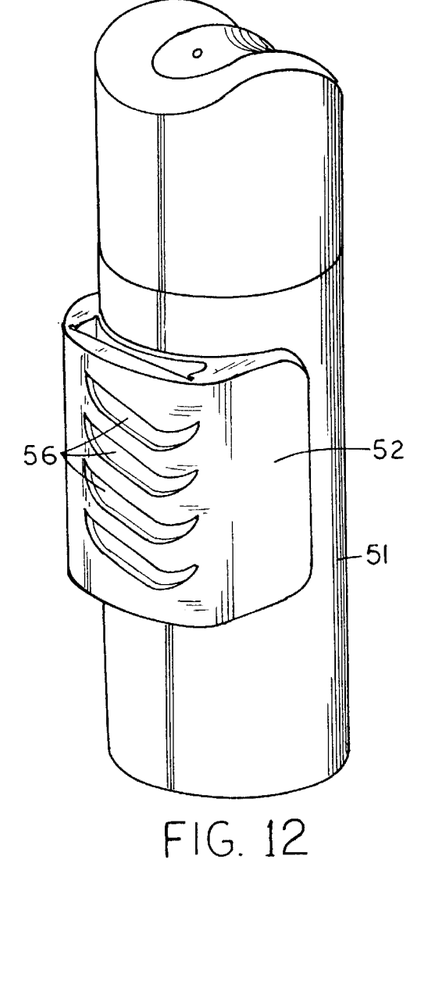
FIG. 12 is a perspective view of a dispenser package of the present invention, comprising an aerosol active dispenser with a clip-on passive dispenser.
Figure 13:
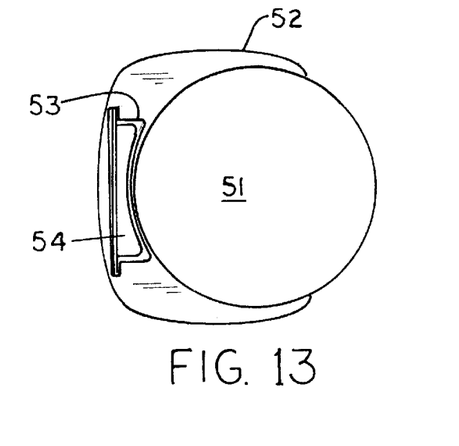
FIG. 13 is a top view of the dispenser package of FIG. 12, showing the relationship of the individual dispenser units.
Figure 14:
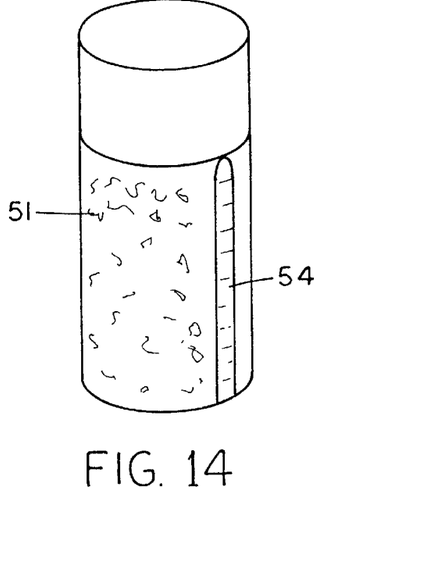
FIG. 14 is a perspective view of a dispenser package comprising an aerosol dispenser with an adhesively attached passive dispenser.

In one embodiment, FIGS. 12 and 13 illustrate a dual capacity dispenser comprising separate active and passive dispenser units, wherein the passive dispenser is removably attached directly to the exterior circumference of the active spray container. In this manner, the consumer may readily replace one or the other dispenser without replacing both. As shown, a conventional spray container, 51, such as an aerosol air freshener, may be provided with a clip-on collar type of passive dispenser, 52. Such a clip-on dispenser may readily be fashioned of economical materials, such as plastic, having sufficient elasticity that it may readily be forced over the diameter of the spray container. Advantageously, as shown in FIG. 13, such a clip-on dispenser may comprise a slot, opening, or receptacle, 53, for positioning a gel cartridge dispenser 54, or other passive dispenser, preferably in juxtaposition to vent openings 56 in said clip-on dispenser, which permit circulation of air into and away from the passive dispenser, 54. Alternatively, the passive dispenser may simply comprise a single gel dispenser cartridge, 54, which may be directly attached to the surface diameter of the spray container, 51, or other form of active dispenser, by such means as an adhesive backing, as shown in FIG. 14. As such an externally applied dispenser, the passive dispenser may take the form of a gel dispenser, an impregnated plastic strip, a saturated porous medium, a plastic container of the "break to activate" type, or any other suitable form of passive release medium, suitably adhered to or attached to the active dispenser.

Figure 15:
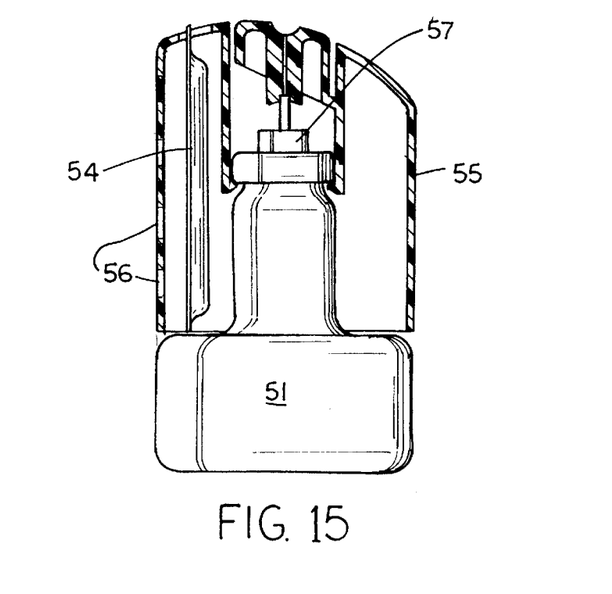
FIG. 15 illustrates a cross sectional view of an alternative form of dispenser package.

Still further, the passive dispenser means may be incorporated directly into the cap or cover of an active dispenser, such as shown in FIG. 15. This type of active dispenser comprises a spray dispenser 51, such as an aerosol dispenser, and refill cartridges therefore, with the outside cap or shell having the passive dispenser, in the form of a gel dispenser, for example, built directly into the shell, inserted therein, or attached thereto. This type of dispenser could be very similar in appearance to the dispenser of FIG. 1, but with the passive dispenser being a separate unit, a part of the shell or cover rather than part of a dual refill unit. As shown in FIG. 15, spray dispenser 51 is encompassed or fitted with a dispenser cap, 55, having interactive relationship with the spray mechanism, 57 of the spray dispenser. A gel cartridge, 54, or other passive dispenser, is fitted into a receiving pocket or slot in the dispenser cap 55, so as to place the evaporative surface area thereof in juxtaposition with vent openings 56, in the dispenser cap.

Figure 16:
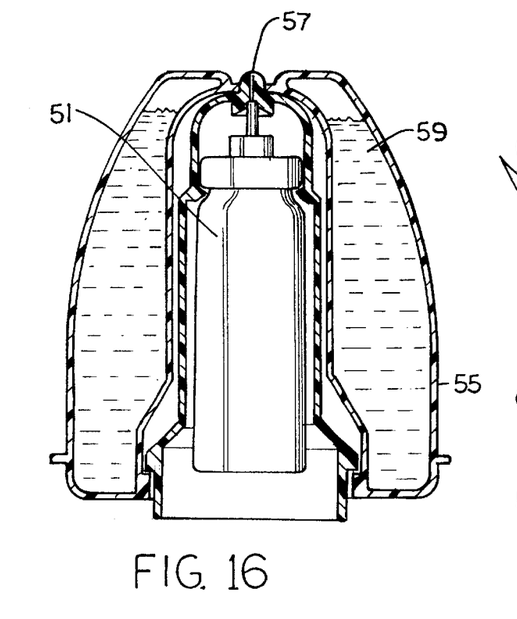
FIG. 16 illustrates a cross sectional view of another form of dispenser, incorporating a solid passively dispensed dispersible.
Figure 17:
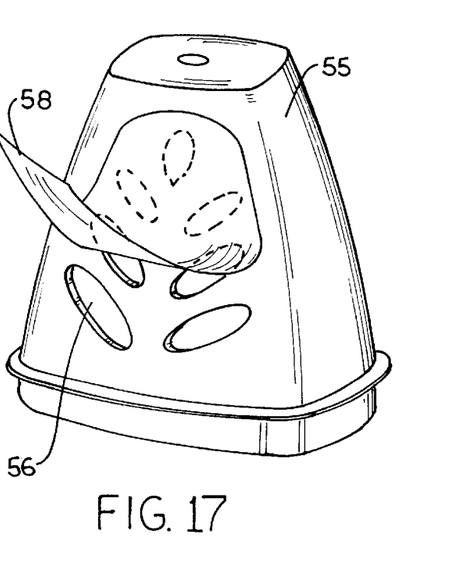
FIG. 17 illustrates a perspective view of the dispenser package of FIG. 16, showing the removable barrier film.

Still another embodiment is shown in FIGS. 16 and 17, wherein the overcap 55 is, in itself, a container or reservoir for a solid, liquid or gel passive dispersible, 59. In this case, the impermeable barrier 58 may be external to the vent openings, 56, in the shell or overcap. The overcap may be provided with one or more vent areas, 56, which are sealed by the peelable or removable impermeable barrier 58 when provided to the ultimate consumer, who then may choose to open one or more of said vent areas to obtain the desired level of dispensing of passive dispersible. As in the previous embodiment, the overcap 55 may be designed so as to fit over and cooperatively engage the spray dispensing means 57 of a spray dispenser can, 51. In this type of dispenser, merely pushing downwardly on the overcap or shell will activate the spray dispensing means, providing a burst of active dispersant. In such an embodiment, the consumer may replace either or both of the active dispensing means (the spray container and spray dispensing means assembly) and the passive dispensing means (the overcap, containing the passive dispersant) at any given time. Since each dispensing means may, contain one of a number of different dispersants, a large number of alternatives are available to the consumer.

Figure 18:
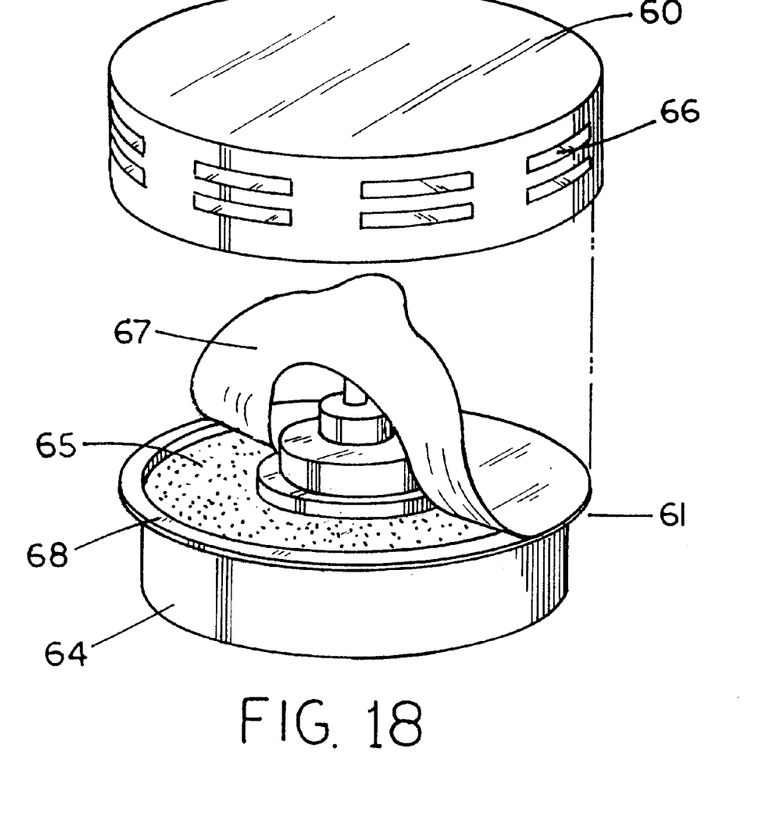
FIG. 18 illustrates a low profile dispenser in exploded view.
Figure 19:
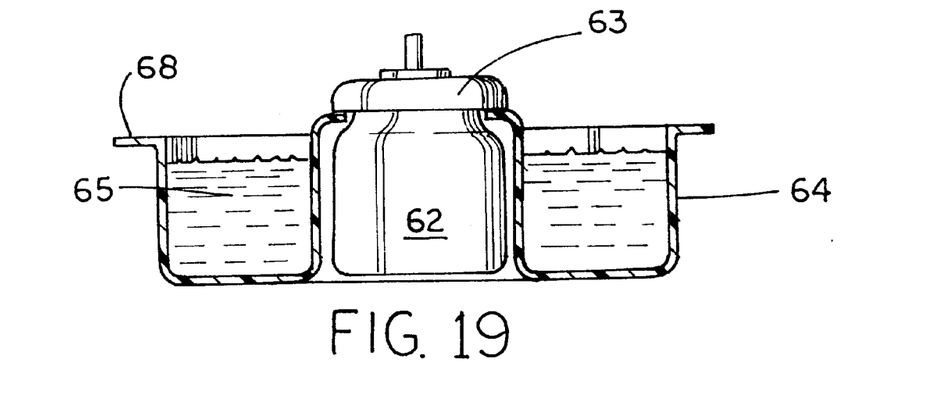
FIG. 19 illustrates a cross sectional view of the low profile dispenser package of FIG. 18.

Similarly, the dual capacity dispenser may take the form of a low profile dispenser, comprising a low tray or container of passive dispersible partially or entirely encircling or encompassing an active spray container, as shown in FIGS. 18 and 19. In this embodiment, a low profile top housing, 60, having vent openings 66 about all or part of its periphery, is fitted over a low profile passive dispenser, 61, which encompasses a central spray dispenser, 62. As with the previously discussed embodiment, the top housing, 60, may cooperatively engage the spray dispenser mechanism 63 of the spray dispenser, such that merely pushing downwardly on said top housing will cause a burst of active dispersible to be released. The top housing may be removably attached to the passive dispenser, 61, such as by threading, clip action, compression fit, or other conventional joining means which permit ready removal. The passive dispenser, 61, comprises a container, 64, preferably having a low profile, which contains a passive dispersible 65. The passive dispersible may constitute a solid, a liquid, or a gel, and is protected by a peel away foil 67 or impermeable barrier which is adhered to the top flange 68 of the container 64.

In addition to the above-described embodiments, other appropriate arrangements combining an active dispensing means and a passive dispensing means will be apparent to one skilled in the art. For example, a bellows means for expulsion of saturated air would constitute a suitable active dispenser, since it is dependent upon an action of the consumer to deliver dispersible material to the atmosphere, while saturation of the air to be dispensed may be accomplished by evaporation of a passive dispersible. Further, passive dispensers may be considered to include such means as heated substrates which are impregnated or saturated with a liquid passive dispersible, as well as heated gel cartridges, solid dispersibles, or the like. Still further, passive dispensers may be combined with such air flow means as fans, either spring driven or electric, to increase the distribution of passively dispensed dispersibles. Active dispensers are understood to include pumps, aerosols, propellant driven dispensers, and bladder contraction means or bellows. In addition to the dual capacity dispensers described hereinabove, the invention includes dispensers having both active and passive dispensers wherein the passive dispenser is heated and/or subjected to forced air flow, such as in a battery operated or plug-in unit, wherein said unit also comprises a button or nozzle activated dispenser, i.e. an active dispenser. Such a dispenser would be of particular interest for such locations as a kitchen counter, where it could be plugged into a wall outlet for enhanced passive provision of an air freshener, while remaining available for a spray discharge of an actively dispersed material such as a fragrance or deodorizer.

Typically, an ingredient suitable for inclusion in the evaporative cartridge, or passive dispenser, for the present invention is a fragrance, air freshener, deodorizer, odor eliminator, malodor counteractant, insecticide, insect repellant, medicinal substance, disinfectant, sanitizer, mood enhancer, aroma therapy composition, or the like, in liquid or gel form, although gels are preferred for the present invention. Preferably, the fragrance or air freshener is a fragrance comprising one or more volatile organic compounds which are available from perfumery suppliers such as Firmenich Inc., Takasago Inc., Noville Inc., Quest Co., International Flavors & Fragrances, and Givaudan-Roure Corp. Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like. A fragrance can be relatively simple in composition, or can be a complex mixture of natural and synthetic chemical components. Synthetic types of fragrance compositions either alone or in combination with natural oils are described in U.S. Pat. Nos. 4,324,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobomyl acetate, and the like.

A liquid fragrance may also be formed into a thixotropic gel by the addition of a thickening agent, such as a cellulosic material, a polymeric thickener, or a fumed silica of the type marketed under the Cabosil trademark by Cabot Corporation. A fragrance ingredient can also be in the form of a crystalline solid, which has the ability to sublime into the vapor phase at ambient temperatures. A crystalline fragrance starting material can be selected from organic compounds which include vanillin, ethyl vanillin, coumarin, tonalid, calone, heliotropene, musk xylol, cedrol, musk ketone benzophenone, raspberry ketone, methyl naphthyl ketone beta, phenyl ethyl salicylate, veltol, maltol, maple lactone, proeugenol acetate, evemyl, and the like. This type of fragrance can contribute a long term air-treatment capability to an air freshener dispenser device for use in the present invention. Many of such fragrances are also suitable for adaptation to be used in the spray dispensing mode of the present invention.

EXAMPLE 1

A dual function air freshener was prepared in the configuration of FIG. 1, using an active liquid spray unit comprising a complex floral fragrance, comprising Takasago RE 3792/E, and a passive time release cartridge having a gel therein comprising a companion fragrance, Takasago RI 1962/2. The liquid dispenser had a dose metering valve such that the refill unit was capable of spraying 90 measured sprays of the air freshener. The gel cartridge, after removal of the impermeable membrane covering the gel, released air freshener for a period of about 30 days, with a vent opening area in the shell of approximately 48 percent of the area of exposed gel. It was found that in normal usage, both the spray dispenser and the gel dispenser were essentially exhausted or empty after about 30 days.

EXAMPLE 2

A dual function dispenser was prepared in accordance with the configuration of FIG. 1, having a spray dispenser of Takasago RE 3792/E fragrance, and a vapor dispenser comprising a long term dispenser of Takasago RI 1962/2 fragrance. This dispenser was compared to a Glade® Plug-In dispenser having the same fragrance as the passive dispenser, for a 30 day period, and found to have greater utility in that an instant effect of the fragrance was readily available from the active mode of the dual capacity dispenser. The passive dispenser, with a 47% venting area, was found in acceptance testing to be "too strong" after 3 days by 3 percent of evaluators, while the plug-in was found to be "too strong" after 3 days by 19 percent. Conversely, the passive mode of the dual capacity dispenser was evaluated as "just right" by 88 percent, while the plug-in was so evaluated by 79 percent. After 30 days, the passive mode of the dual capacity dispenser was considered "just right" by 58 percent, and "too weak" by 37 percent of evaluators, while the plug-in was considered "just right" by 67 percent, and "too weak" by only 19 percent of the evaluators. These evaluations reflect the fact that the dual capacity passive mode dispenser was nearing complete loss of dispersible material at the end of 30 days, while the plug-in unit had a larger amount of dispersible material remaining and continued to dispense such material at a higher rate than the other.

EXAMPLE 3

A spray unit dispenser of a deodorizer composition is combined with a passive dispenser of air freshener attached thereto by a clip-on collar. By spraying of the deodorizer, the consumer may address malodors or smoke as desired, while the passive dispenser of the air freshener creates a background atmosphere of a pleasant scent.

EXAMPLE 4

A dual capacity refill unit was prepared, comprising a spray dispenser of a complex floral fragrance, with a twin gel cartridge unit comprising a gel form of a companion fragrance. Upon exhaustion of the dispenser reservoirs of Example 1, this dual capacity refill unit was placed in the shell to replace the exhausted active and passive dispensers. The dispenser unit was then available for continued use for an additional period of time.

EXAMPLE 5

A single gel cartridge comprising a complex floral fragrance is prepared, and used to replace only the passive dispenser in the clip-on collar of the dual capacity dispenser of Example 3, illustrating the freedom of the consumer to replace one dispenser without replacement of the other.

EXAMPLE 6

A dual capacity dispenser is prepared for insect control. A spray dispenser of insecticide is encircled with a low profile container of a volatile insect repellant. The volatile material is covered by a foil, which is removed for activation of the insect repellant. This dispenser is suitable for use as a long-term insect repellant dispenser, with a spray unit for rapid attack upon insects if they should appear to the consumer.

EXAMPLE 7

A spray can of sanitizer is prepared as an active dispenser, incorporating an odor eliminator in the overcap as a passive dispenser. An aerosol air sanitizer, comprising triethylene glycol plus a suitable fragrance as the dispersible sanitizer spray, with a standard spray valve, is combined with a charcoal odor absorber, in the form of particulate carbon glued to a woven backing to maximize air flow. This dual capacity dispenser is found to have great utility in the kitchen and bath areas.

From the above discussion, and the Figures, it may be seen that the present invention comprises a dual capacity or dual use dispenser for dispersible ingredients, such as a fragrances or air fresheners. By dual use or dual capacity, it is meant that at least two differing modes of distribution are included and utilized in a single dispenser apparatus, and that the two are independent of each other. In the preferred embodiment, the dispenser apparatus comprises an active, short term, or immediate provider, such as a spray dispenser, in conjunction with a long term or time effective passive dispenser of the evaporation mode, i.e. a container of an evaporative medium.

Relative to the short term, or spray medium, it is preferred that metered dosage spray containers be used, so that controlled amounts of medium are released at any given time of use. In this manner, a predetermined number of sprays, or applications, may be provided for, by predetermination of the volume of the spray container, the pressurization thereof, and the volume of medium released with each spray application by the consumer. In this manner, one may predict, based upon statistical analysis of typical consumer utilization, the life expectancy of the spray unit, and accordingly select a long term or evaporative component of the dual capacity dispenser to have a similar life expectancy, at normal or ambient temperatures of consumption. In such a manner, when both modes of dispensing are exhausted at approximately the same time, the consumer is most likely to note and react to the need for refill or replacement of the dispenser. It is a preferred embodiment of the present invention that the spray container and evaporative medium container, preferably a gel container, be replaced at the same time, in the form of a dual capacity refill unit, comprising both a spray container and a gel container of the same or complementary air fresheners or fragrances. Such refill units may be provided as a unitary structure or package for simultaneous purchase, or may be provided as complementary structures or packages for separate purchase by the consumer for later combination and insertion into the shell or shroud of the dispenser, which need not be replaced upon exhaustion or consumption of the contents thereof. As is the case of the "Lasting Mist®" dispenser device commercially available from S. C. Johnson & Son, Inc. of Racine, Wis., the dispenser of the present invention may comprise a body that accepts a replaceable cartridge, which a user or consumer inserts into an open cartridge receptacle. Thus, the dispenser may be configured so as to accept a refill unit comprising a mated set of replacement units for the spray container and the gel or evaporative medium container, or, alternatively, the dispenser may be configured so that spray container and evaporative medium container may be replaced independently of each other. It is understood that by the term "independently of each other", the simultaneous replacement of both units is not precluded, but that it is intended that the consumer has the option to replace either or both of the spray container and the evaporative medium container at any given time, and that replacement of both at one time is neither required nor precluded.

Spray containers suitable for use with the present invention may, in general, comprise an aerosol or pump dispenser can comprising a containment volume for the medium to be sprayed, and a valve stem which communicates with a spray nozzle orifice of the dispenser. Said can may be activated by actuation means included in the dispenser shell or shroud into which the can may be inserted for use, or the spray container may come complete with actuation means, e.g. a spray nozzle assembly, for use with alternate dispensers. The spray container may be provided with a spray medium of choice, selected from the various spray media available, such as fragrances, insecticides, medicinals, etc, under pressure within the containment vessel, generally a metallic cannister of the type well known in the art. A valve stem and nozzle orifice are provided, providing a fluid communication between the pressurized media in the can, and with the spray tip through which the pressurized media can escape from the valve stem. The spray delivery system further includes valve means for controlling the release of the pressurized material, into the spray orifice, the valve means being manually operable by the user. Preferably the valve means is a conventional aerosol valve. The preferred valve employed as the means for controlling the release of the pressurized material or media is a valve that delivers a single, metered discharge of pressurized material each time the valve stem is actuated. In any event, the valve means is manually operable by the user of the dual function dispenser. In general, the shell of the dispenser of the present invention is so shaped as to be conveniently and comfortably held in the hand of the user when it is desired to employ the spray medium. However, it is also desired that the shell of the dispenser be so shaped as to be decorative and non-intrusive, so that it may be left in plain view for dispensing of the evaporative medium. Thus, the shell of the dispenser, and the dispenser means associated therewith, may comprise a shell which is simply pressed downwardly to activate the spray mechanism, while the dispenser is left in view on a counter or table top, as a decorative item which acts as a passive dispenser of the same or a different material as is dispensed by the spray.

Although it is possible for the aerosol can and associated hardware to be permanently mounted within the shell or shroud of the dispenser of the invention, it is preferred instead that inner surfaces of the dispenser shell be so configured that the aerosol can, its associated valve stem, and the evaporative media container and related structures may comprise a single unit which is removable from the shell and replaceable by a refill unit comprising like elements.

An advantage of the present invention is the constant release of an air freshener, for example, from the evaporative cartridge, or passive dispenser, which thus provides a constant and long-term effect, while the consumer may, at his or her option, increase the effect of the said air freshener by actuating the spray container to obtain additional air freshener or fragrance, for example, as desired or required. It is also considered within the scope of the present invention to utilize differing compositions for the active spray component and the passive component, to provide differing effects. For example, the spray component might be an odor eliminator, to allow one to overcome offensive odors such as in a kitchen or bathroom, while the passive dispenser could be a perfume, to provide a pleasant ambient scent to a room or given area when serious offensive odors are not present. Similarly, one may provide a spray dispenser of an insect repellant or insecticide, in conjunction with a long-term passive dispenser of insecticide or insect growth regulator.

It is also to be understood that the term volatile material as used in conjunction with the passively dispersed dispersant, is intended to refer to a material which is subject to evaporation or vaporization as its primary means of distribution. This is not to imply that the actively dispersed materials may not be "volatile" in the normal sense of the word, since such materials as perfumes and fragrances are obviously volatile. The distinction to be drawn is that distinction between active dispersement and passive dispersement, with the term volatile reserved herein to refer to those materials which are passively dispensed, i.e. those which are dispersed by vaporization or volatilization.

Further, when it is indicated that the actively dispensed material and the passively dispensed material may be "the same", it is not intended to imply that the two are chemically identical, but that the two may belong to the same class or group of suitable materials, such as to indicate that both are fragrances, both are sanitizers, both are insecticides, and so forth. As previously indicated, it is well known that a given specific composition may not function well as both a passive dispersant and as an active, or sprayed, dispersant. However, when it is indicated that the actively dispensed material and the passively dispensed material "differ", it is intended to imply that the two are not chemically identical, but not to preclude the possibility that both belong to the same class or group of dispersants. Thus, it is possible that the active and passive dispersibles may differ, but may both be fragrances, for example.

While the present invention has been described with respect to what are at present considered to be the preferred embodiments, it is to be understood that the invention is not to be limited to the disclosed embodiments. For example, the disclosure has been exemplified in terms of fragrances and air fresheners, while it is clear that other dispersible materials, such as insect repellents, and other dispersibles mentioned hereinabove may be utilized. Accordingly, the invention is intended to cover various modifications and equivalent arrangements within the spirit and scope of the appended claims. The scope of the following claims is to be accorded the broadest interpretation so as to encompass all such modifications and equivalent formulations and functions.

INDUSTRIAL APPLICABILITY

The practical usefulness of the dual capacity dispenser and refill cartridges disclosed herein, with respect to the dispensing of dispersible media conventionally delivered by an aerosol delivery system, or by evaporation, including, by way of example only, air fragrancing or insect control dispersible ingredients and the like, will be readily apparent to those skilled in the art. Except for the aerosol can, all the parts described may be made from suitable plastics by conventional molding or other plastic fabrication techniques. The aerosol can may be made in conventional ways from aluminum or other suitable metals, with a conventional metered or unmetered valve means. The evaporative medium container may be made from plastics, metal, paper, ceramic, or laminated stock, or combinations thereof.

We claim:

1. A dual capacity dispenser for dispersible materials, said dispenser comprising the combination of:
   a) an active dispenser for an actively dispersible material, said active dispenser comprising a first reservoir containing said actively dispersible material, and means to actively dispense said actively dispersible material from said reservoir to the atmosphere;
   b) a passive dispenser for a volatile dispersible material, said passive dispenser comprising a second reservoir containing said volatile dispersible material, and means to control volatilization of said volatile dispersible material; and
   c) means to combine said passive dispenser and said active dispenser into a dual function dispenser.

2. A dual capacity dispenser as set forth in claim 1, wherein said dispersible materials are selected from the group consisting of fragrances, air fresheners, deodorizers, odor eliminators, odor counteractants, insecticides, insect repellants, medicinal substances, disinfectants, sanitizers, mood enhancers, and aroma therapy compositions.

3. A dual capacity dispenser as set forth in claim 2, wherein said actively dispersible material differs from said volatile dispersible material.

4. A dual capacity dispenser as set forth in claim 2, wherein said actively dispersible material and said volatile dispersible material are the same.

5. The dual capacity dispenser of claim 2, wherein said active dispenser and said passive dispenser are independently replaceable.

6. A refill unit for a dual capacity dispenser of dispersible materials, said refill unit comprising a first reservoir containing a spray dispersible material, and a second reservoir of volatile passively dispersible material, said second reservoir having a membrane bonded thereto which is permeable to the gaseous form of said volatile passively dispersible material but impermeable to liquid or solid forms thereof and a vapor impermeable membrane bonded to said second reservoir containing said volatile passively dispersible material external to said permeable membrane to prevent volatilization of said volatile passively dispersible material and adapted for removal to permit volatilization of said volatile passively dispersible material.

7. A refill unit as set forth in claim 6, wherein said dispersible materials are selected from the group consisting of fragrances, air fresheners, deodorizers, odor eliminators, malodor counteractants, insecticides, insect repellants, medicinal substances, disinfectants, sanitizers, mood enhancers, and aroma therapy compositions.

8. A refill unit as set forth in claim 7, wherein said first reservoir and said second reservoir may be independently replaced.

9. A refill unit as set forth in claim 8, wherein said actively dispersible material differs from said volatile passively dispersible material.

10. A refill unit for a dual capacity dispenser of dispersible materials, said refill unit comprising a first reservoir containing an actively dispersible material selected from the group consisting of fragrances, air fresheners, deodorizers, odor eliminators, malodor counteractants, insecticides, insect repellants, medicinal substances, disinfectants, sanitizers, mood enhancers, and aroma therapy compositions, said first reservoir adapted to engage a second reservoir comprising a volatile passively dispersible material.

11. A refill unit for a dual capacity dispenser of dispersible materials, said refill unit comprising a passive dispenser comprising a reservoir containing a volatile passively dispersible material selected from the group consisting of fragrances, air fresheners, deodorizers, odor eliminators, malodor counteractants, insecticides, insect repellants, medicinal substances, disinfectants, sanitizers, mood enhancers, and aroma therapy compositions, and means to control volatilization of said volatile passively dispersible material, said refill unit adapted to engage an active dispenser unit capable of independently dispensing an actively dispersible material from an independent reservoir.

12. The refill unit of claim 11, wherein said passive dispenser comprises a gel cartridge having at least two independent compartments.

13. A dual function dispenser, said dispenser comprising a spray dispenser having a first reservoir for a spray dispersible material and means to dispense said spray dispersible material to the atmosphere, a gel cartridge dispenser comprising a second reservoir for a volatile passively dispersible material and means to control vaporization of said volatile passively dispersible material, and means to join said spray dispenser and said gel cartridge dispenser.

14. A dual function dispenser as set forth in claim 13, wherein said spray dispenser and said gel cartridge dispenser independently as desired dispense a dispersible selected from the group consisting of fragrances, air fresheners, deodorizers, odor eliminators, malodor counteractants, insecticides, insect repellants, medicinal substances, disinfectants, sanitizers, mood enhancers, and aroma therapy compositions.

15. A dual function dispenser as set forth in claim 14, wherein said gel cartridge comprises a vapor permeable membrane to permit vaporization of said volatile dispersible material.

16. A dual function dispenser as set forth in claim 15, further comprising means to enhance the vaporization of said volatile dispersible material.

17. A dual function dispenser as set forth in claim 16, wherein said enhancement means comprises a fan.

18. A dual function dispenser as set forth in claim 16, wherein said enhancement means comprises means to heat said volatile dispersible material.

19. A dual function dispenser as set forth in claim 15, wherein said means to join said spray dispenser and said gel cartridge dispenser comprises a shell adapted to hold said dispensers.

20. A dual function dispenser as set forth in claim 19, wherein said shell comprises a passage for said spray dispersible material to reach the atmosphere, and openings for said volatile dispersible material reach the atmosphere.

21. A dual function dispenser as set forth in claim 20, wherein said openings comprise an area corresponding to from about 40 to about 60 percent of the surface area of said vapor permeable membrane.

* * * * *